US00PP13686P29

(12) United States Plant Patent
Heims

(10) Patent No.: US PP13,686 P2
(45) Date of Patent: Mar. 25, 2003

(54) PULMONARIA PLANT NAMED 'MOONSHINE'

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 10/080,061

(22) Filed: Feb. 19, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman LLP

(57) ABSTRACT

A new and distinct hybrid of Pulmonaria plant characterized by a compact habit with short, ovate leaves of heavy substance and silvering, very light violet blue flowers, and excellent mildew resistance.

2 Drawing Sheets

Botanical classification: Pulmonaria hybrid.
Variety denomination: 'Moonshine'.

BACKGROUND OF THE INVENTION

The present invention relates to a new and distinct cultivar of a hardy perennial of the genus Pulmonaria, and known by the cultivar name 'Moonshine'. The genus Pulmonaria is a member of the family Boraginaceae.

The new cultivar originated as an open-pollinated cross between unknown parents which were grown in a field of selected hybrid Pulmonaria. This is known to be an outcross because Pulmonaria does not normally self-pollinate. Due to the fact that the instant plant and parent plants are interspecific hybrids from several generations of interbreeding and selecting, no species designations are given.

SUMMARY OF THE INVENTION

This new plant is characterized by:

1) Compact, rounded form;
2) Short, ovate leaves of heavy substance;
3) Heavy silvering on summer leaves with contrasting green edges;
4) Very light violet blue, almost white flowers;
5) Excellent vigor and resistance to mildew.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
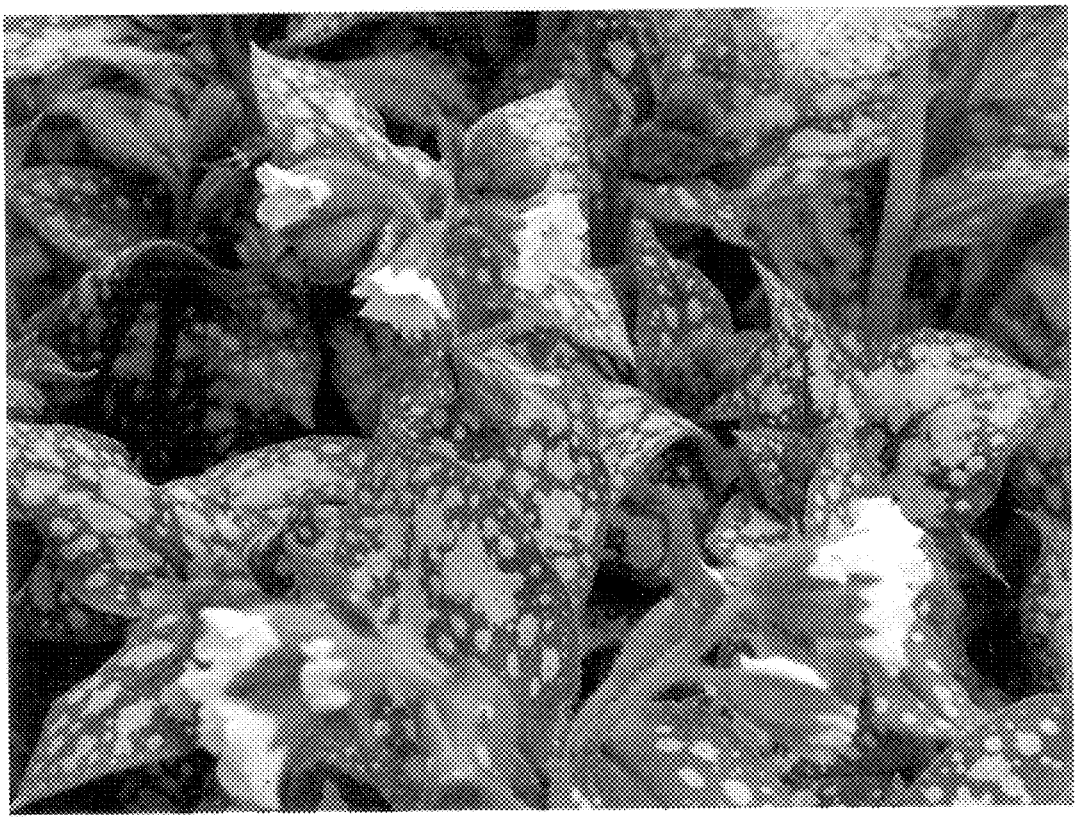
FIG. 1 shows a close up of Pulmonaria 'Moonshine' in flower in the spring.
Figure 2:
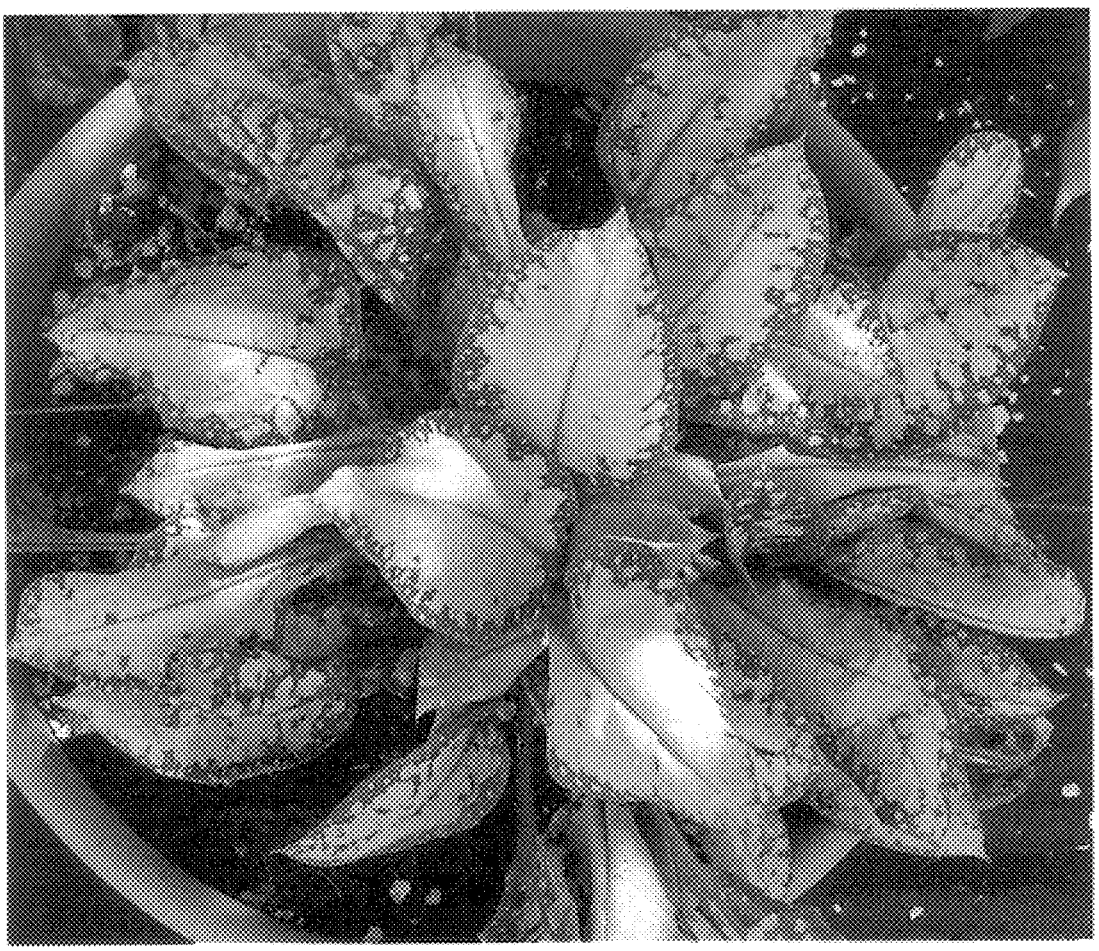
FIG. 2 shows the summer foliage.

The following is a detailed description of the new Pulmonaria hybrid based on observations of one and a half-year-old specimen grown in the ground in Canby, Oreg. The color descriptions are all based on The Royal Horticultural Society Colour Chart.

Botanical name: Pulmonaria hybrid.
Cultivar name: 'Moonshine'.
Plant:
- *Type.*—Herbaceous perennial.
- *Hardiness.*—USDA Zones 5 to 9.
- *Spring size.*—33 cm. wide and 29 cm. tall.
- *Summer size.*—35 cm. wide and 18 cm. tall.
- *Form.*—Basal clump.

Leaf:
- *Type.*—Simple.
- *Shape.*—Ovate to elliptic.
- *Arrangement.*—Rosette.
- *Blade length.*—15 cm.
- *Width.*—8 cm.
- *Margins.*—Entire.
- *Apex.*—Acute.
- *Base.*—Attenuate.
- *Venation.*—Pinnate.
- *Texture.*—Hispid.
- *Aspect.*—Matte.
- *Petiole length.*—12 cm.
- *Petiole texture.*—Sparsely hispid.
- *Petiole color.*—Yellow Green 146C.
- *Color.*—Topside: Deep Green edges, Green 137A, with silver centers, Greyed Green 192A or deep green with silver spots and/or blotches. Bottom: Closest to Green 138B.

Cauline leaves (These are found only in the spring on the flowering stems. After the seed is produced these stems die out.):
- *Type.*—Simple.
- *Arrangement.*—Alternate.
- *Shape.*—Variable. Obovate to ovate.
- *Length.*—3 to 5.7 cm.
- *Width.*—2.7 cm.
- *Margins.*—Entire.
- *Apex.*—Acute.
- *Base.*—Clasping, sessile.

*Leaf texture.*—Hispid.
*Venation.*—Pinnate.
*Color.*—Topside: Deep green, Green 137A with ¾ of the leaf covered with silver spots and blotches, Greyed Green 193B. Bottom side: Closest to 191A.

Inflorescence:
*Type.*—Terminal forked cyme.
*Number of flowers per cyme.*—17.
*Peduncle.*—Height: 28 to 33 cm. Diameter: 3.5 to 4 mm. Texture: Hispid. Color: Yellow Green 146C.
*Pedicel.*—Length: Varies. 0.1 to 0.4 cm. Texture: Hispid. Color: Yellow Green 146C.

Flower bud:
*Size.*—1 cm. long and 0.4 cm. wide, with 0.4 cm. of corolla exposed.
*Shape.*—Ovoid.
*Color.*—Light pink, Red Purple 69A.

Flower:
*Type.*—Actinomorphic.
*Shape.*—Funnelform with petal lobes ruffled.
*Size.*—1 to 1.2 cm. deep and 1 to 1.2 cm. wide.
*Corolla.*—5 fused petals with rounded lobes.
*Color.*—Changes with age from light pink, Red Purple 69A in the newly opened flowers, to light violet blue, Violet Blue 91C, in the mature flowers.
*Calyx.*—5 fused sepals, tublular campanulate, parted ⅓ to base, hispid and glandular hairy.
*Calyx size.*—1.1 cm deep and 0.6 cm wide.
*Calyx color.*—Green 137B.
*Pistil.*—0.9 cm. long, pin type, exerted from corolla tube.
*Ovary position.*—Partly inferior.
*Carpel number.*—4.
*Stamen number*—5, attached to and inserted in the tube.
*Pollen color.*—White 155A.
*Bloom period.*—Late February to late April in Canby, Oreg.
*Fragrance.*—None.

Seed:
*Type.*—4 smooth nutlets, Black 202A and shiny, typical of the genus.
*Fertility.*—Low.

Disease: None observed on plant grown under commercial conditions in Canby, Oreg.

COMPARISONS TO SIMILAR PULMONARIA

Compared to Pulmonaria 'Excalibur' (U.S. Plant Pat. No. 8,958), Pulmonaria 'Moonshine' has a more compact habit, much lighter flowers, and smaller, rounder leaves.

Compared to Pulmonaria 'Silver Streamers' (U.S. Plant Pat. No. 12,135), this new cultivar has a more compact habit, much lighter flowers, smaller, rounder leaves, and more green on the leaf and leaf margins.

Compared to Pulmonaria 'Baby Blue' (U.S. Plant patent application Ser. No. 10/080,060), this new cultivar has a more compact habit, smaller, lighter colored flowers, and more silvering on the leaves.

I claim:

1. A new and distinct hybrid of Pulmonaria plant substantially as shown and described, characterized by a compact habit with short, ovate leaves and very light violet blue flowers.

* * * * *